United States Patent [19]
Bitterly

[11] Patent Number: 4,756,310
[45] Date of Patent: Jul. 12, 1988

[54] SYSTEM FOR COOLING AN AREA OF THE SURFACE OF AN OBJECT

[75] Inventor: Jack G. Bitterly, Woodland Hills, Calif.

[73] Assignee: Hemodynamics Technology, Inc., Newbury Park, Calif.

[21] Appl. No.: 673,509

[22] Filed: Nov. 19, 1984

Related U.S. Application Data

[63] Continuation-in-part of Ser. No. 383,004, May 28, 1982, Pat. No. 4,569,355.

[51] Int. Cl.$^4$ ............................................... A61F 7/00
[52] U.S. Cl. .................................... 128/400; 128/403; 62/50; 62/514 R
[58] Field of Search ............................... 128/399–400, 128/402–403, 736; 62/514 R, 50

[56] References Cited

U.S. PATENT DOCUMENTS

| Re. 30,317 | 7/1980 | Lubbers et al. | 128/635 |
|---|---|---|---|
| 2,551,650 | 5/1951 | Urbach . | |
| 2,982,132 | 5/1961 | Mendlowitz . | |
| 3,479,838 | 11/1969 | Bitterly . | |
| 3,587,577 | 6/1971 | Smirnov et al. | 128/402 X |
| 3,882,687 | 5/1975 | Asztalos et al. | 62/514 R X |
| 3,933,149 | 1/1976 | Salera et al. | 128/736 |
| 3,967,627 | 7/1976 | Brown | 128/400 |
| 3,995,621 | 12/1976 | Fletcher et al. | 128/400 X |
| 4,129,432 | 12/1978 | Garside | 62/514 R X |
| 4,175,543 | 11/1979 | Suzuki et al. | 128/736 |
| 4,191,197 | 3/1980 | Benzinger | 128/736 |
| 4,228,805 | 10/1980 | Rosen et al. | 128/691 |
| 4,332,136 | 6/1982 | Quack | 62/514 R X |
| 4,348,873 | 9/1982 | Yamauchi et al. | 62/514 R X |
| 4,364,398 | 12/1982 | Sassi et al. | 128/736 |
| 4,495,988 | 1/1985 | Grossman | 62/514 R X |
| 4,548,053 | 10/1985 | Brown | 62/514 R X |

OTHER PUBLICATIONS

Green et al.; "A Lg. High Current Density Superconducting Solenoid for the Time Projection Chamber Experiment"; Conf: Proc. of 7th Int'l Cryogenic Engr. Conf; 7-1978, pp. 86–98.

Primary Examiner—Edward M. Coven
Assistant Examiner—Angela D. Sykes
Attorney, Agent, or Firm—Poms, Smith, Lande & Rose

[57] ABSTRACT

A device for cooling a small area of skin over several cycles is used to measure the condition and efficiency of the capillary bed in returning the skin temperature to normal. The system has a heat exchanger which is attached to the skin. Controlled amounts of a low-boiling point liquid are injected into a cooling chamber. One side of the chamber has conductive material, which against the skin. The heat of the skin boils the liquid, which in turn cools the heat conductive material and the skin. A wick help carries the liquid to the heat conductive surface. A vessel stores the liquid. A movable divider separates the vessel into two spaces. The low-boiling point liquid is stored on one side of the divider. The second space contains a fluid having a significant higher vapor pressure then the first-mentioned fluid so that the pressure from the second fluid pressurizes the first fluid, keeps it in liquid state and drives it to the heat exchanger. Flow is controlled by a valve mounted in the heat exchanger. In another embodiment, an intermediate injector or valve receives low-boiling point liquid from the vessel and passes it to the heat exchanger in response to signals from a computer. The computer is also fed with temperature signals in the skin to maintain a skin temperature within the measuring band-width. The heat exchanger is also useful in other systems such as generalized body cooling in high-temperature environments.

48 Claims, 8 Drawing Sheets

SYSTEM FOR COOLING AN AREA OF THE SURFACE OF AN OBJECT

BACKGROUND OF THE INVENTION

1. Related Applications

This application is a continuation-in-part of my copending application Ser. No. 383,004 filed May 28, 1982 entitled "Method and Apparatus for Monitoring and Diagnosing Peripheral Blood Flow," now U.S. Pat. No. 4,569,355 (Feb. 11, 1986).

2. Field of Invention

The present invention relates to an apparatus for monitoring blood flow automatically by cooling a small area of skin through several cycles and monitoring the rate at which the internal blood flow returns the skin to normal temperature. The cooling device which the blood flow monitor uses also can be used for general cooling of the body in high-temperature environments.

3. Description of Prior Art and Patent Application

Parent U.S. Pat. No. 4,569,355 discloses that changes in blood flow can be monitored by cooling an area of skin terminating the application of cold and measuring the rate at which the internal blood flow raises the skin temperature. The rate of temperature change is a function of the efficiency of the circulatory system which supplies the capillaries in the immediate area of the skin. By cycling through alternating cooling and non-cooling cycles, involuntary constrictive muscles of the blood vessel arterioles begin to fatigue. The capillaries in healthy people return the skin temperature toward normal faster.

The parent application discusses one way of manipulating the data to yield a Cardio-Thermal Index or CTI. The CTI can be used for absolute readings for comparing circulatory efficiency in one person relative to another, or the individual can be his or her own control using the present invention to monitor changes in blood flow at a given "healthy" location as related to a vascular diseased area.

When one uses the device of the present invention to show changes over relatively long periods of convalescent time in a patient, the device can show the effectiveness of treatment and/or the prognosis. The present invention can be used for many other purposes. It can determine changes in peripheral vascular disease ("PVD"). As PVD increases, it is desirable to be able to diagnose these changes so that effective treatments or corrective surgery can be initiated or changed. Although present pharmacological treatments have been of limited value in treating PVD, new drugs are the subject of continuing current investigation, and it will be necessary to monitor subtle improvements in blood flow to test the efficacy of the new medications and to determine in the particular patients whether the drugs or other corrective measures are having their desired effect.

An unfortunate consequence of impaired blood flow is tissue damage, which, if it becomes too pronounced, can ultimately require limb amputation. The present invention can predict, based on a predetermined CTI, where on a limb an amputation should take place so that the area of the amputation receives sufficient blood flow for healing. It can also indicate that amputation is not needed and corrective surgery can be instigated negating the permanent and drastic effects of amputation. After amputation, the blood flow near the wound can be monitored non-invasively to determine whether the flow is sufficient for healing and whether the amputation site was properly chosen.

The accuracy of the method of monitoring blood flow is improved by precise controls of the cooling heat exchanger and its related instrumentation. The heat exchanger relies on injecting a low-boiling point liquid into a cooling chamber against the skin. The body heat boils the heat exchanger liquid thereby transferring some of its heat energy to vaporizing this liquid, which in turn cools the skin and the capillary bed. As set forth in the parent application, temperature recovery when there is no further liquid in the heat exchanger is slower in a person with PVD. In the parent application, a relatively complex structure was devised for accurately controlling injection of the low-boiling point liquid into the heat exchanger chamber. It is an object of the present invention to provide precise control for the amount of liquid entering the heat exchanger. Another object of the present invention is to provide this controlled cooling in a highly reliable instrument.

It is desirable that the cooling unit be small. The cooling unit in the parent application is designed to be relatively small, but the unit that is applied to the skin incorporates structure for determining the controlled amount injected into the heat exchanger. Thus, there are parts on the unit adjacent the skin that move. Without due care, the complex unit may lead to discomfort and inaccuracies in the readings as the movements of the unit and its own weight may have an effect on circulation at a localized test area.

It is not always necessary to locate all parts of the injector near the heat exchanger. The heat exchanger may be connected to parts of the injector through a line. The low-boiling point liquid in the line is essentially incompressible. A valve that opens at a predetermined, high pressure and is located in or near the heat exchanger can maintain the liquid in the line up to the predetermined pressure. Raising the pressure in the line by adding a controlled volume of liquid at the upstream end of the line causes the liquid at the downstream end of the line to be injected past a minute check valve into the heat exchanger. If the valve is upstream from the heat exchanger, the vapor pressure of the liquid causes liquid in the line between the valve and the heat exchanger to flow slowly into the heat exchanger. The slow flow of liquid lowers the pressure in the line, which may allow the liquid to boil in the line, which is undesirable. It is an object of the present invention to improve the valving to eliminate potential problems.

The liquid that is present at the upstream end of the line at the injector must also be fed to the injector at a controlled pressure. One of the purposed low-boiling point liquid is a fluorinated hydrocarbon sold under the trademark Freon$_{114}$. This liquid, however, has a relatively low vapor pressure on the order of 28 psi (115 cm of Hg). For proper utilization the heat exchanger fluid should be stored at higher that its own vapor pressure. High pressure storage is important because as ambient temperature varies up or down, its vapor pressure follows the same signum direction. With storage at higher than vapor pressure, the liquid pressure can be regulated down to a constant outlet pressure, which will always be higher than vapor pressure at any reasonable ambient temperature. This allows fluid supply to the heat exchanger to be at a constant pressure. It is an object of the present invention, therefore, to provide a system that permits a low-boiling point and low-vapor pressure liquid such as Freon$_{114}$ to be utilized accurately in the present invention.

Various fail-safe systems are also provided so that if insufficient pressures develop, the device will shut down rather than yield an incorrect answer.

These objects, as well as others that will be evident in the remainder of the specification, are accomplished by the blood flow monitor of the present invention. It includes a heat exchanger attached to the object to be cooled (i.e. the skin). The heat exchanger operates by having the low-boiling point liquid injected against a thin, conductive surface. Normally, this surface is at approximately skin temperature. When the low-boiling point liquid strikes the surface, it boils, which cools the surface. Cooling ceases when all of the liquid in the heat exchanger boils off. In theory, heat from the skin boils the liquid. This heat flux cools the skin. Because the liquid changes phase, the heat flux from the skin to the liquid is great, and skin cooling is rapid. Surface film boiling heat transfer is manyfold greater than liquid heat transfer and is therefore presumed to be the best system.

The liquid is held in a container, which is connected to the heat exchanger by tubing or other connecting means. In one embodiment, a pressure sensitive valve at the downstream end of the connecting means at the heat exchanger normally blocks the flow of liquid from the source to the heat exchanger except when the pressure of the liquid at the pressure sensitive valve is greater than a predetermined pressure. Control means, which may be high speed valve or a small pump in the connecting means upstream from the pressure sensitive valve, normally blocks the connecting means. In response to a signal, the control means passes or injects a controlled amount of liquid to the line leading to the pressure sensitive valve instantly at a pressure no lower than the predetermined pressure so that the pressure sensitive valve instantly passes the liquid into the heat exchanger where it vaporizes and cools the heat exchanger surface and the skin.

As previously mentioned, the control means for controlling the flow of liquid to the heat exchanger may be a high speed valve that opens and closes very rapidly to allow a precise volume of liquid to pass from the source to the heat exchanger. When the valve opens, the incompressible liquid downstream from the valve is raised to an elevated pressure above the pressure necessary to permit the pressure sensitive valve to open. The pressure sensitive valve opens, and the volume of liquid that flows past the high speed valve also flows past the pressure sensitive valve into the heat exchanger. In another version of this embodiment, the control means is a pump or variable volume injector that receives a controlled volume of liquid and pumps it into the connecting means upon receiving a signal. The pump raises the pressure at the pressure sensitive valve so that the volume of liquid pumped is equal to the volume injected past the valve pressure sensitive valve into the heat exchanger.

In the other embodiment, a miniaturized solenoid valve is mounted within the heat exchanger. The valve normally blocks liquid from entering a small orifice, which when open, allows the liquid to be directly injected by impingement onto the surface of the heat exchanger where boiling takes place. Upstream from the valve, the liquid is maintained at the predetermined pressure by means to be described. By adjusting the period and frequency at which the solenoid-controlled valve stays open, the amount of cooling that the heat exchanger provides can be modified.

The solenoid valve embodiment also has a system for adjusting the solenoid valve without disassemblying the entire heat exchanger.

The source of liquid is a container divided into two compartments by a movable wall. One of the compartments contains the low-boiling point liquid, for example, Freon$_{114}$. The other compartment contains a small volume of liquid having a very much higher vapor pressure, and the remainder of the compartment, a much larger volume, contains the gas phases of the liquid. Freon$_{12}$, a trademark for a fluorinated hydrocarbon, is one such liquid. The vapor of the higher vapor pressure liquid transmits pressure forces through the movable wall to pressurize the lower vapor pressure liquid to approximately the vapor pressure of the higher vapor pressure gas. As long as some of the higher vapor pressure material in the liquid state remains in its compartment, that compartment will be at equilibrium at the higher pressure. As the volume of the remaining low-boiling point liquid Freon$_{114}$ in the other compartment decreases (no gas is present in this compartment as it is above the vapor pressure point) to the point that insufficient liquid may be left for a single test, the system triggers a release valve and all reserve material and its gas will be vented to the atmosphere so that no liquid (in short supply) can be used by the system. Thus, inaccurate readings are avoided on a partially completed test. Furthermore, the automatically emptied container can now be safely shipped for refurbishment and refilling. cl BRIEF DESCRIPTION OF THE DRAWINGS

FIGS. 3 and 4 are a side views, in section of the FIG. 2 heat exchanger embodiment of the present invention. FIG. 3 is taken through plane 3—3 and FIG. 4 is taken through plane 4—4 in FIG. 2 and shows the ballonet in place.

DETAILED DESCRIPTION OF PREFERRED EMBODIMENT

1. The System in General: The system for cooling an area of the surface of an object of this invention is shown in schematic in FIG. 1. Heat exchanger 10 is attachable to the object. Container 120 is a source of a primary liquid having a boiling point below room temperature at standard atmospheric pressure. Connecting means (lines 222 and 260 in FIG. 1) between the source of primary fluid and the heat exchanger transports the primary fluid from the source to the heat exchanger. In one embodiment, a solenoid 53 activates a plate 57, which covers orifice 55. In the normal, closed position, the plate blocks the orifice and prevents the primary fluid from being injected into cooling chamber 76. When the solenoid is activated, orifice 55 is uncovered, and liquid is injected into chamber 76. Computer controller 280 can change the frequency and duration of the solenoid's open position to control the rate at which the skin temperature changes.

In another embodiment for the heat exchanger (FIG. 5), a pressure sensitive valve 354 between the connecting means and the heat exchanger blocks flow of primary fluid from the source to the heat exchanger except when the pressure of the primary fluid at the pressure sensitive valve means is no lower than a set, predetermined pressure. A control valve 226 (phantom in FIG. 1) (or pump 228 in FIG. 11) in the connecting means upstream of the pressure sensitive valve means normally blocks the connecting means. In response to a signal, valve 226 allows a controlled amount of primary fluid to flow in the connecting means toward the pressure sensitive valve 354 at a pressure no lower than the predetermined pressure. The amount of liquid flows past control valve 226 also flows past pressure sensitive valve 354 into the heat exchanger where the primary liquid vaporizes to cool the surface of the object.

Figure 2:
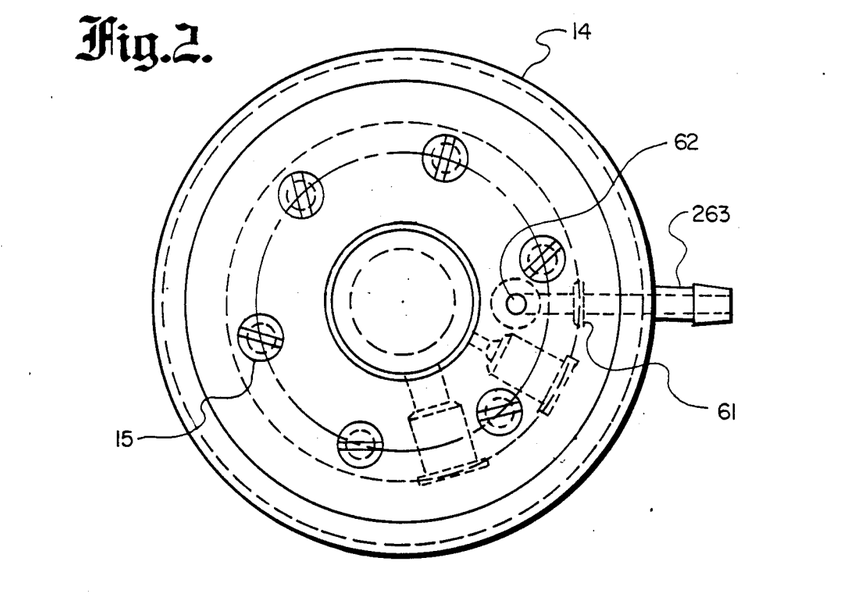
FIG. 2 is a top view of one embodiment of the heat exchanger of the present invention. The adjusting screw is not shown.
Figure 3:
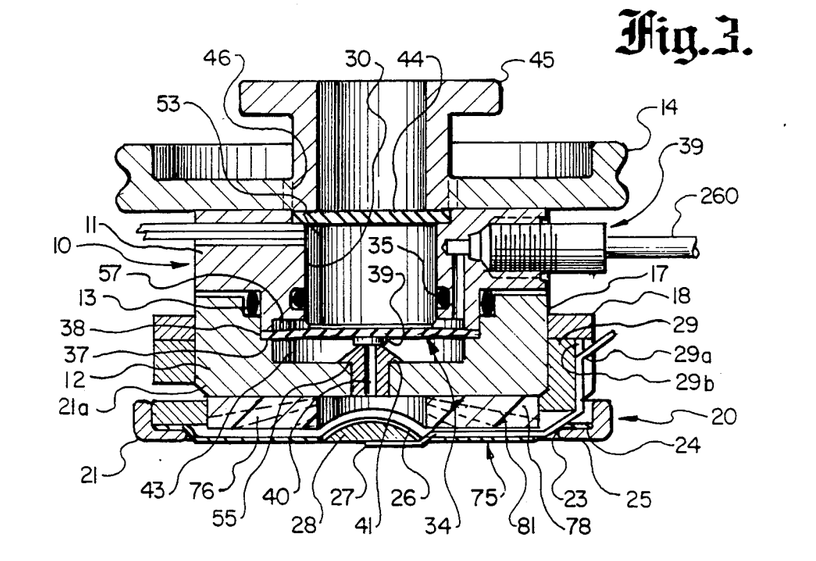
Figure 4:
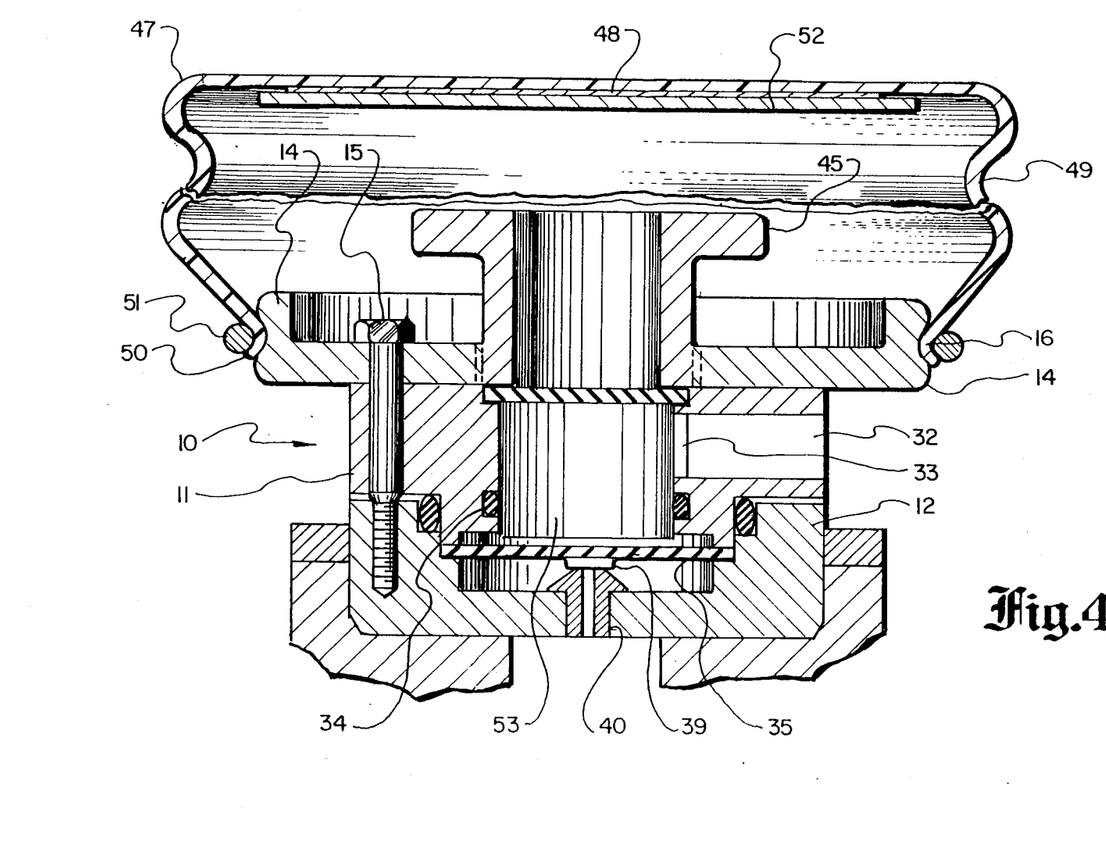

2. The Heat Exchanger: The system for cooling an area of the surface of an object of the present invention includes a heat exchanger attached to the object. The details of two principal embodiments are disclosed. The first embodiment, heat exchanger 10 (FIGS. 2, 3 and 4), are described first. Heat exchanger 10 has a hard plastic body 11 and an orifice assembly 12, which are attached together and are sealed by O-ring 13. FIGS. 3 and 4 shown that body 11 and diaphram assembly 12 fit together to create certain spaces, which are discussed in more detail below. Bolts 15 extend through cover 14, through body 11 and into orifice assembly 12 where they are tapped to hold body 11 and orifice assembly 12 together and to secure cover 14 on top of body 11 (FIGS. 2 and 4). Outer wall 17 of orifice assembly 12 is threaded, and a nut 18 (FIG. 3) is threaded up on the outside of orifice assembly 12. Next a plastic ring 19 is threaded to outside wall 17 of orifice assembly 12, and lastly an outer ring 20 is threaded up the same surface to hold ring 19 in place. Plastic nut 20 has a curved, smooth surface 21. It is this surface in part that will be against the patient's skin. Sharp edges would not be desirable. For a point of reference, the diameter of ring 19 is about 1.4 in (34 mm).

Ring 19 supports the cooling surface that is against the skin and that forms the cooling chamber between the cooling surface and the bottom of orifice assembly 12. The cooling surface assembly comprises diaphragm 75, so named because it is formed of thin, flexible material. In the exemplary embodiment, diaphram 75 is formed of a high, heat conductive material. The exemplary embodiment uses 0.002 in (0.05 mm) thick stainless steel. Although higher heat coefficient materials are available (e.g. gold or copper), stainless steel is stronger, and it is thin enough that heat will be readily transferred. As best seen in FIG. 3, the outside edge of diaphram 75 has a small bend 23, and the outside edge 24 is supported by inwardly facing flange 25 of nut 20 and secured against the bottom surface of ring 19. This insures that the diaphram and its supporting ring nut will be flush with and not indent the skin.

Diaphram 75 is generally flat except at the center where it curves upward at 26 to receive a thermocouple 27, which is separated by a small piece of insulation 28. Thermocouple 27 is electrically connected to the computer by lead 29a (FIG. 3). For ease of assembly lead 29a is short and terminate onto slip rings 29b contained within ring 18. These slip rings are safe for thermocouples as long as they are made of the same respective materials as the lead wires 29. The remainder of lead 29 may run parallel with one or more of the lines that carry the refrigerant in the present invention. Insulation 28 is provided so that thermocouple 27 reads true skin temperature and is isolated from diaphram 75 which is a cold surface.

The space between the bottom of orifice assembly 12 and diaphram 75 is a cooling chamber 76 (FIG. 3). For support of the thin diaphram 75, most of cooling chamber 76 contains a high void 3-D plastic material 78 such as that sold under the trademark Trilock. The material allows liquids and vapor to pass generally freely through it.

Central opening 30 of body 11 receives an electromagnet/solenoid 53 (FIGS. 2-4). Electromagnet 53 is secured by set screw 32 in body 11 (FIG. 4), which urges pad 33 against the outside of electromagnet 53. O-ring 35 helps seal the electromagnet in the body.

Tube connector assembly 39 is threaded radially into body member 11 (FIG. 3) and it attaches tube 260, which carries the primary, low-boiling point liquid to the heat exchanger.

Solenoid clapper 34, which is a spring, extends from circumferential slot 38, which is formed between body 11 and orifice assembly 12. Shims 37 may be provided to secure clapper 35 in slot 38. Normally, clapper 35 urges attached pad 39 down to cover the top of orifice 40. As is explained below, orifice 40 is the only inlet to cooling chamber 76. Orifice 40 is formed by a thin aluminum tube extending through plastic seat housing 41, which is press fitted into an opening of orifice assembly 12. With the parts positioned as shown in FIGS. 3 and 4, pad 39 blocks orifice 40 preventing the flow of liquid into cooling chamber 76. Clapper 35 is mounted in such a way that pad 39 normally closes the top of orifice 40.

Primary fluid flows through tubing 260, tube carrier 34 and into passage 42 (FIG. 3). From there, the liquid flows into delivery chamber 43, but it cannot flow through orifice 40 because the top of the orifice is sealed by pad 39. Clapper 34 has several openings through it around the periphery to allow the liquid to flow to all parts of delivery chamber 43. When electromagnet 53 is energized, the clapper is attracted upward to the electromagnet, which momentarily uncovers the top of orifice 40 and allows the primary liquid to flow into cooling chamber 76. The liquid is under pressure, so it flows at a relatively high velocity out of orifice 40 through void material 78. The liquid strikes wicking material 81 attached to the top of diaphram 75, and it is heated by the skin. The high velocity jet and the wick allows the heat exchanger to operate in any position and is not affected by gravity. Therefore its operation is valid on any position on the patient's body. The liquid boils causing a rapid heat flux through the diaphram, which, in turn, cools the skin under the diaphram rapidly. The vaporized liquid escapes through radial openings 212 (FIG. 3) through ring 29. To help distribute the liquid evenly on the surface of diaphram 75, threads 81 of wick-type material such as wettable fabric or paper may permeate void material 78 to conduct the liquid to the diaphram.

When the solenoid shuts off, electromagnet 53 releases clapper 34, and the clapper returns to its original position with pad 39 sealing the top of orifice 40.

The flow of liquid can be adjusted in several ways. First, by way of a permanent adjustment, the diameter of orifice 40 determines the rate of flow through the orifice. In the preferred embodiment, the diameter of 40 ranges from 0.001–0.020 in (0.025–0.50 mm). Because of variations between the orifices of "identical" seat housings, flow must be adjustable if two units are to perform identically. This can also be done by the computer control whereby it sets the pulse width and/or its frequency. The cooling characteristics may only be known after assembly of the unit, and it is costly and may not be effective to experiment with different seat housings in an attempt to find identical ones. Therefore, the present invention provides a means adjusting the actual amount of liquid passing through orifice 40.

Normally, the flow would also be controlled by changing the duration that electromagnet 53 was activated. Rather than have electromagnet activated for a specific, adjustable length of time, the present invention can adjust the pulse width and the frequency at which energizing pulses are sent to the electromagnet.

If the distance that the clapper moves in response to a magnetic pull from electromagnet 53 changes, the length of time that orifice 40 remains uncovered changes. Therefore, the present invention also provides a means for adjusting the relative distance between clapper 35 and electromagnet 53 to change the time per pulse that orifice 40 is uncovered. This in effect changes the spring preload of clapper 35. As previously stated, electromagnet 53 is positioned and held in central opening 30 of body 19 by a set screw 32 (FIG. 4). When the set screw is loosened, pressure forces from the fluid act upward on the bottom of electromagnet 53 will tend to urge the electromagnet upward. The top of electromagnet 53 is in contact with thin plate 44, which in turn is in contact with an adjusting screw 45. The screw is threaded into central opening 46 of cover 14 (FIGS. 3 and 4). The electromagnet 53 moves upward until it contacts plate 44, which is against the bottom of adjusting screw 45. By rotating adjusting screw 45 in one direction, electromagnet 53 can be allowed to move upward; rotating the adjusting screw 45 in the opposite direction pushes the electromagnet closer to clapper 35.

The solenoid valve is designed to work very rapidly. Therefore, the normal distance between clapper 35 and the bottom of electromagnet 53 is approximately 0.005 in (0.12 mm). For these precise distances, an extremely fine thread is used to hold screw 45 in cover 14.

Once what is believed to be the preferred location for solenoid 53 is set, set screw 32 is then tightened, and the heat exchanger is ready to be tested. If under test it is determined that slight changes are necessary, the adjustment process can be repeated several times until the heat exchanger operates as desired.

Before discussing further operation of the system, the second heat exchanger embodiment (FIG. 5) is discussed. Heat exchanger 310 comprises a body 311 having internal cavities shown in FIG. 5 and described below. The inside wall 317 of ring 313 is threaded such that ring 313 can be threaded to outside threads of body 311. Outer ring 329 is threaded on ring 313. The outer rings 329 supports the heat transfer disk in a manner similar to the support in the first embodiment (FIGS. 2–4) and described below. Body 311 and rings 313 and 330 are made of plastic. Ring 313 has a number of spaced radial holes 315 (FIG. 5), which permit vaporized gas to escape. Outer edge 325 of bottom surface 323 of 330 is rounded because it is intended to be against the skin. In the exemplary embodiment the outside diameter of inner ring 313 is 1.25 inches (31.8 mm). (Metric equivalents are approximate.) An aluminum alloy locking nut 327 with a threaded inside surface is also threaded on outside threads of body 311. When nut 327 is tight against ring 313, the nut and ring are held tightly on body 311 in the orientation shown in FIG. 5.

Figure 5:
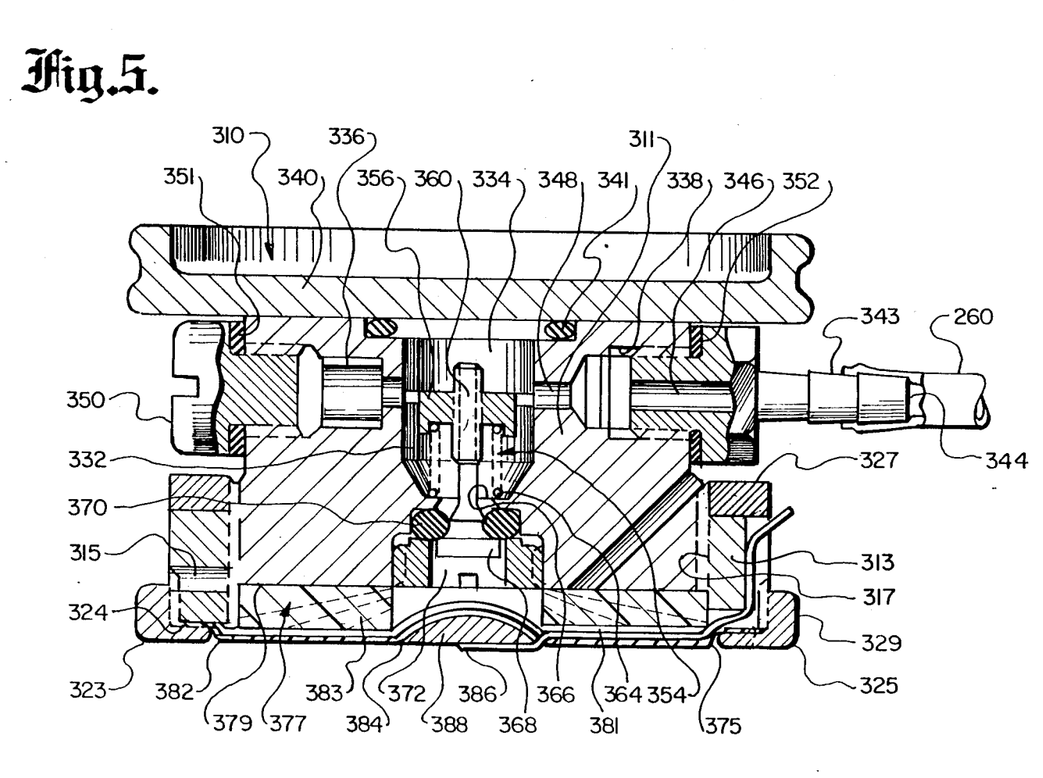
FIG. 5 is a side view in section of the heat exchanger of a second embodiment of the present invention.

Body 311 also has a central cavity 332 and three openings 334, 336, and 338 (FIG. 5). Cover 340 sealed by O-ring 341 closes the top opening. Hose fitting 343 is threaded into opening 338 on the right side of the body. The hose (260) that ultimately attaches to the source of low-boiling point liquid is attached to end 344 of fitting 343. The liquid flows through opening 346 extending through fitting 343. Opening 346 is aligned with aperture 348, which extends into central cavity 332. Plug 350 is threaded into opening 336 on the left side. Removing or loosening plug 350 bleeds air or gas from the system. O-rings 351 and 352 seal plug 350 and fitting 343 to body 311, respectively.

Part of a pressure sensitive valve assembly 354 is mounted within central cavity 332. This valve assembly includes a retainer 356, which is fixed to poppet assembly 360 (FIG. 5). The bottom end of helical spring 364 is mounted against the bottom wall 366 of opening 334, and the top portion of spring 364 pushes against retainer 356 to urge the retainer and the poppet assembly upward. This upward force causes valve closure member 368, which is part of the poppet assembly, to seat against o-ring 370 at the top of the injection opening 372. As long as upward forces from spring 364 exceed the downward fluid pressure forces on the top of valve closure member 368, the member stays seated against o-ring 370. The force acting downward on member 368 is a function of the area of the member that is exposed to the pressurized liquid (a constant) and the pressure of the liquid itself (a variable).

As explained in more detail below, precisely measured quantities of low-boiling point liquid at a predetermined pressure enter a hose (260 in FIG. 1) connected to hose fitting 343. If pressure sensitive valve 354 is at equilibrium, (i.e. the liquid pressure force acting downward on member 368 is no greater than but almost equal to the upward spring force on member 368), valve 354 stays closed and no liquid flows. If the liquid pressure acting downward on member 368 exceeds the opposite force from spring 364, which occurs when a measured quantity of liquid is forced to enter line 260, the valve opens. Liquid flows through valve 354 until the pressure above the valve drops sufficiently to permit spring 364 to close the valve. If the system was initially in equilibrium, the volume of liquid flowing past valve 354 should be equal to the volume of liquid added to hose 260. If the pressure in central cavity 332 is initially much less than the pressure needed to open valve 354, several "shots" of liquid are added to the hose until valve 354 opens for the first time. An operator or sensors feel the first cooling from the heat exchange when liquid first passes valve 354. Because the liquid is not compressible and there is no compressible gas in the line (bleed through outlet 336 or injected through the valve in the original "shots"), by controlling the volume of liquid entering the hose upstream from the heat exchanger, the same volume of liquid should be injected past check valve 354 into injection opening 372.

This embodiment also uses a thin disk 375 of high-heat conducting material, which is also supported between upper shoulder 330 of nut 329 and under the bottom surface 324 of ring 313 flush with surface 323 of nut 329. Items within the chamber (FIG. 5) are discussed below. The low-boiling point liquid injected past pressure sensitive valve 354 travel through chamber 377 of the exchanger created between disk 375 and bottom wall 379 of body 311 and strikes disk 375.

As in the earlier mentioned embodiment, a wick in the form of radial threads 381, which extend to an optional wicking disk 382 distribute the low-boiling point liquid evenly around disk 375. Light weight void material 383 helps support the thin material of disk 375, causes the disk to remain flat but does not interfere significantly with the passage of fluid through the material to the wicks and disk.

Opening 384 (FIG. 5) is provided at the center of disk 375. The void material also has an opening above opening 384. Thermocouple 386 and its insulation 388 are mounted at opening 384. The thermocouple (or some other temperature sensing device) reads the skin temperature. Insulation 388 shields the thermocouple from the cooling effects of the low-boiling point liquid so that the thermocouple only "reads" skin temperature. The thermocouple is connected to a controller 280 by wire 389 that preferably runs along the tubing 260 (FIG. 1) that is connected to end 344 of fitting 343.

3. Holding the Heat Exchanger to the Skin: A ballonet, which is attached to a band (FIGS. 4 and 13 described below) and to cover 14 or 340 is part of a system for attaching the heat exchanger to the skin. The ballonet is an inflatable device, which pushes against the band and the heat exchanger to urge the heat exchanger against the skin at a controlled pressure of approximately 13 mm of Hg. With lower pressure, the cooling disk 75 or 375 may make incomplete contact with the skin. At higher pressure, the disk may constrict the blood vessels to a slight degree and affect the readings.

The ballonet is used in both embodiments, but it is shown and discussed only in reference to FIG. 4 of the first embodiment. Ballonet 47 is made from flexible, rubber-like material and has a generally flat top surface 48 and bellows-like sides 49. Bottom portion 50 of sides 49 fit into channel 16 extending around the circumference of cover 14. An O-ring 51 or other securing device holds the bottom of ballonet 47 to cover 14. As an alternative, ring 51 could be incorporated into the ballonet. A semi-rigid disk 52 is cemented within ballonet 47 to the bottom of top surface 48 to add rigidity to that surface and to prevent bulging.

The ballonet is fed with air through line 262 (FIG. 2), which runs parallel to line 260 and which is attached to a compressor and a very low pressure regulator (not shown). The air is received by fitting 61 in body 11. Opening 62 (FIG. 2) leads from body 11 through cover 14 into the ballonet. The air then pressurizes the ballonet. A small compressor and strict pressure regulator insures that the pressure in line 263 and inside ballonet 47 is maintained at approximately 13 mm of Hg.

Figure 13:
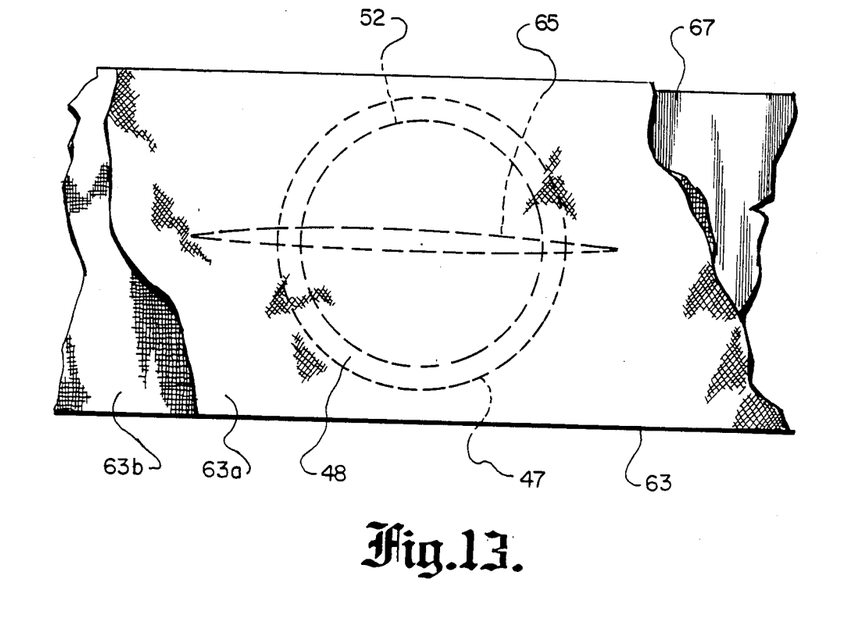
FIG. 13 is a top, cut away view of the band for attaching the heat exchanger of this invention to the skin.

Disk 52 makes the top part of ballonet 47 fairly rigid so that the ballonet can be attached to various devices for holing heat exchanger 10 on the skin. A sleeve of fabric 63 (FIG. 13) has an outer piece of fabric 632 and a inner piece of fabric 636. A slit 65, similar to a button-hole, is made in the inside piece of fabric. Slit 65 receives disk 52 at top 48 and a short portion of side wall 49 of ballonet 47, which are all inserted as a button would be inserted into any button-hole. An alternate to the slit is to deform the fabric hole into an ellipse whose major axis is slightly larger than disc 52, thus allowing insertion. The ends (not shown) of sleeve 61 are attached together around a limb such that the cooling disk of the heat exchanger is held loosely against the skin. The sleeve should be placed such that there is some room between the top of ballonet 47 and the top of cover 45. When the ballonet pressure is turned on the gap is filled and the heat exchanger sensor is automatically held to the skin at a predetermined pressure (i.e. 13 mm Hg). If the heat exchanger is not going to be mounted to a limb, sleeve 60 can be provided with an aluminum or other light weight flexible sheet 67 (FIG. 13). The sheet can be bent to conform to part of the body to support sleeve 61 and heat exchanger 10. For example, a portion could be bent over the shoulder so that the heat exchanger would position itself over an area of the chest. When ballonet 47 is filled with air at its controlled pressure, the top of the ballonet pushes against sleeve 61, and the bottom pushes against the skin as the controlled pressure.

4. The Vessel: The heat exchanger unit just described uses a low-boiling point liquid for rapidly lowering the temperature of the heat exchanger and thus the skin in a controlled manner. The preferred fluid is Freon$_{114}$, although other refrigerant-type liquids and mixtures are acceptable. Freon$_{114}$ has a boiling point at standard pressure of about 39° F. (4° C.). Freon$_{114}$, however, has a low vapor pressure at room temperature of approximately 28 psi (114 cm of Hg). This relatively low vapor pressure makes it difficult to use the pressure for moving and controlling liquid. For example, a low pressure liquid will pass slowly through valve 354. The valve must stay open longer for the same volume, the liquid will not move as easily to disk 75 or wick 81, and the system will work more slowly.

Freon$_{12}$, on the other hand, has a higher vapor pressure, about 90 psi (465 cm of Hg) at room temperature, but its boiling point (well below 0° F.) and vaporization characteristics are not appropriate for the heat exchanger of the present invention. The high vapor pressure of Freon$_{12}$ is used in the present invention to pressurize the Freon$_{114}$ so that the "better" liquid can flow through the system at a higher pressure. By maintaining the Freon$_{114}$ at an elevated pressure, it remains in its liquid state until it is injected into the heat exchanger where it can boil. Therefore, it is important that the pressure on the Freon$_{114}$ be sufficiently higher than its vapor pressure to keep the liquid from boiling upstream of the heat exchanger.

The present invention utilizes a new rechargeable vessel for dispensing fluid at the controlled pressures for the present invention. In the exemplary embodiment, vessel 120 (FIGS. 6-8) is cylindrical and vessel is formed of two aluminum alloy sections 122, 124, which mate together in a conventional manner at flanges 126 and 128. The two flanges are held together by bolts 132.

Figure 7:
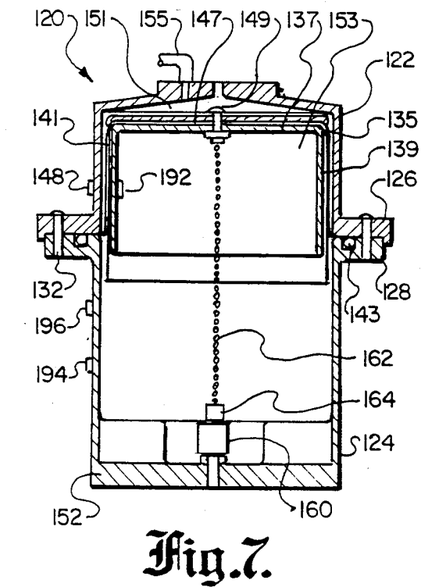
FIGS. 7 and 8 are front sectional views of the container of the present invention. The volume of the upper portion of the container is at a minimum in FIG. 7; there is substantial volume to the upper portion of the container in FIG. 8.
Figure 8:
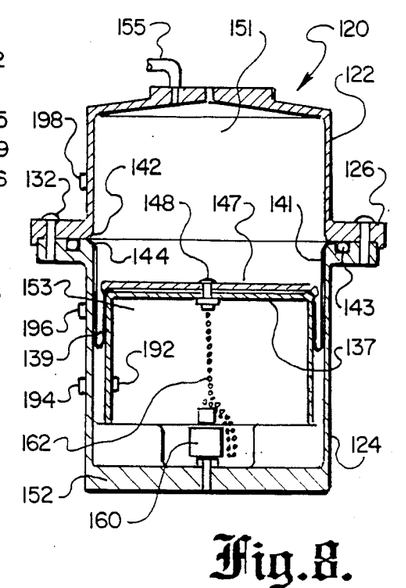

Movable divider means are provided in vessel 120 for dividing the vessel into first and second spaces. In the exemplary embodiment the divider is in the form of a diaphragm and piston. In FIGS. 7 and 8, aluminum piston 135 has a generally horizontal portion 137 and a cylindrical vertical wall 139. Diaphragm 141 extends over horizontal wall 137 of piston 135 and extends into the space between flanges 126 and 128. A circumferential notch 142 on lower flange 128 receives outside ring 144 of the diaphragm. Retainer 147 is above diaphragm 141 and holds the central portion of the diaphragm to the top of piston 135. Bolt 149 extends through the piston, diaphragm and retainer to hold the three parts in place. The combined piston-diaphragm, divides the interior of vessel 120 into an upper portion 151 and a lower portion 153. As the amount of liquid in the upper portion 151 changes, the piston-diaphragm moves.

In the exemplary embodiment, upper portion 151 contains $Freon_{114}$; (liquid phase only) lower portion 153 contains $Freon_{12}$ in gas and liquid phase. As long as any liquid $Freon_{12}$ remains in the lower portion of the vessel, that portion will be at the vapor pressure of $Freon_{12}$, approximately 90 psi. The pressure pushes piston-diaphragm 135/141 upward against the lower vapor pressure liquid $Freon_{114}$ in upper portion 151 of the vessel so that the $Freon_{114}$ is also at 90 psi. At this higher pressure, the $Freon_{114}$ remains liquid. The $Freon_{114}$ in upper portion 151 of vessel 120 flows through outlet 155 (FIGS. 1, 7 and 8) toward the heat exchanger (FIGS. 2–4 or 5) via a pressure reducing regulator thus assuring that the supply fluid to the heat exchanger is only liquid and always the same pressure, which is independent of temperature. The amount of $Freon_{12}$ loaded initially in lower portion 153 is equal to the amount of liquid, which, when vaporized, yields enough gas to fill the inside of vessel 120 with a minuscule amount of liquid remaining in lower portion 153.

In the exemplary embodiment, vessel 120 has an approximately 4 inch (10 cm) inside diameter and a 6 inch (15 cm) inside height, which yields an inside volume of approximately 75 in³ (1236 cm³), disregarding the volume taken up by the internal parts.

Figure 6:
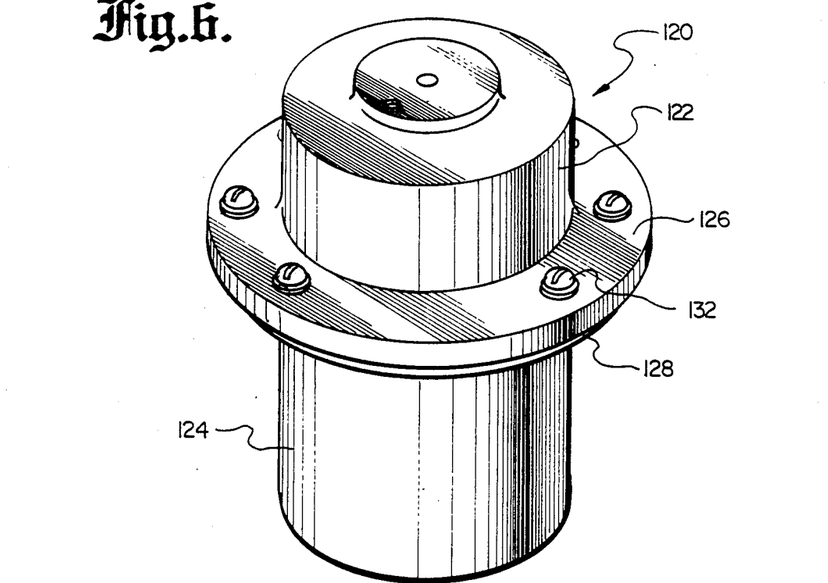
FIG. 6 is a front perspective view of the container that acts as the source of the low-boiling point liquid in the present invention.

Instead of the combined piston-diaphragm arrangement disclosed in FIGS. 6 and 7, a single piston with O-rings against the inside of the vessel can also be used. It would be mounted axially within vessel 120 such that the outside of piston would extend to the inside walls of the vessel. O-ring seals would prevent co-mingling of the liquids.

Either of the piston-diaphram or piston alone arrangement can be used with a working fluid volume sensor. In the exemplary embodiment a permanent magnet 192 is affixed to the inner wall of the piston (FIG. 8 such that its magnetic field transmits through the nonmagnetic (aluminum) walls 139 of piston 135 and vessel 120. With the container fully filled (FIG. 8), an external sensor such as magnetic operated reed switch 194 in a position to indicate a full tank senses magnet 192. Several other reed switches 196, 198 are also installed indicating, for example (but not limited to), 50% full and 5% full. Each reed switch is connected to appropriate pilot lights indicating working fluid volume present and/or to other feed-back controls.

It is undesirable to start a test if the amount of $Freon_{114}$ remaining in upper portion 151 is insufficient to complete a test. If the vessel 120 runs out of $Freon_{114}$, the system may not recognize this fact immediately. Therefore, the system may yield incorrect results initially. Also, although the $Freon_{12}$ attempts to maintain the $Freon_{114}$ at the greater 90 psi vapor pressure, when the piston-diaphragm combination reaches it uppermost position (FIG. 7), the $Freon_{12}$ will be unable to transfer its pressure to the $Freon_{114}$.

Figure 10:
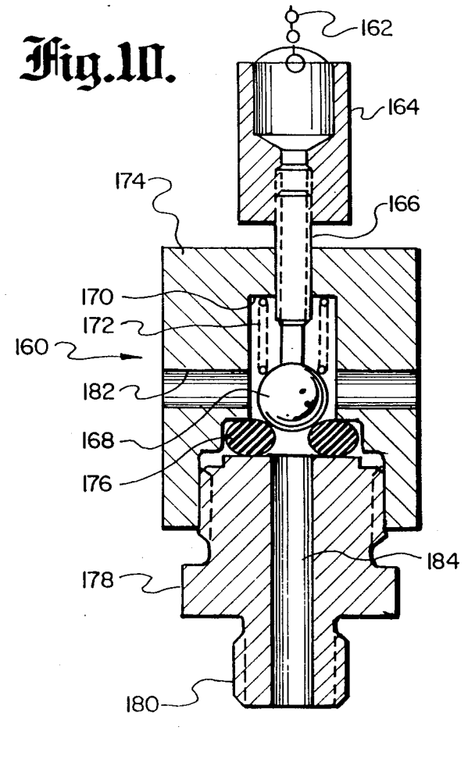
FIG. 10 is a sectional view of a relief valve at the base of the container.

To prevent mistaken readings when the piston-diaphragm reaches its upper-most position (FIG. 7) the present invention automatically releases gaseous $Freon_{12}$ from lower portion 153. This is accomplished in the present invention by means of a relief valve 160 (FIGS. 7, 8 and in detail in FIG. 10) at the base of vessel 120. A non-twisting ball chain 162 or another flexible non-twisting member extends between bolt 149 and fitting 164 of relief valve 160. The chain hangs loosely when the piston-diaphragm is in its lower position (FIG. 8). As the piston-diaphragm rises, chain 162 tightens (FIG. 7) until at its top-most position, chain 162 pulls on fitting 164. The fitting is attached by shaft 166 (FIG. 10) to ball valve closure member or ball 168. Spring 170 mounted within cavity 172 of valve body 174 holds valve closure member 168 against O-ring seat 176. Insert 178 supports O-ring seat 176 (FIG. 10). Section 180 of insert 178 extends through bottom wall 157 of vessel 120. The outside is threaded to receive a nut to secure relief valve 160 to the bottom of the vessel.

When the upward force from chain 162 acting through shaft 166 on ball 168 is greater than the restoring force of spring 170 acting on the ball, the ball rises allowing gas in bottom portion 153 of vessel 120 to flow through inlets 182 into the bottom portion of cavity 172 and out through central opening 184 in insert 178 where it is vented out of the vessel. This immediately relieves any external pressure on the working liquid in upper portion 151 of the vessel. The working fluid now drives the piston down due to its vapor pressure. As the pressure drops, the working fluid vaporizes thus exposing outlet 155 to the gas phase. The gas cannot cool the skin and the computer can sense presence of gas. The computer signals test failure and shuts down the system, which cannot properly function. This prevents getting erronious results.

Figure 1:
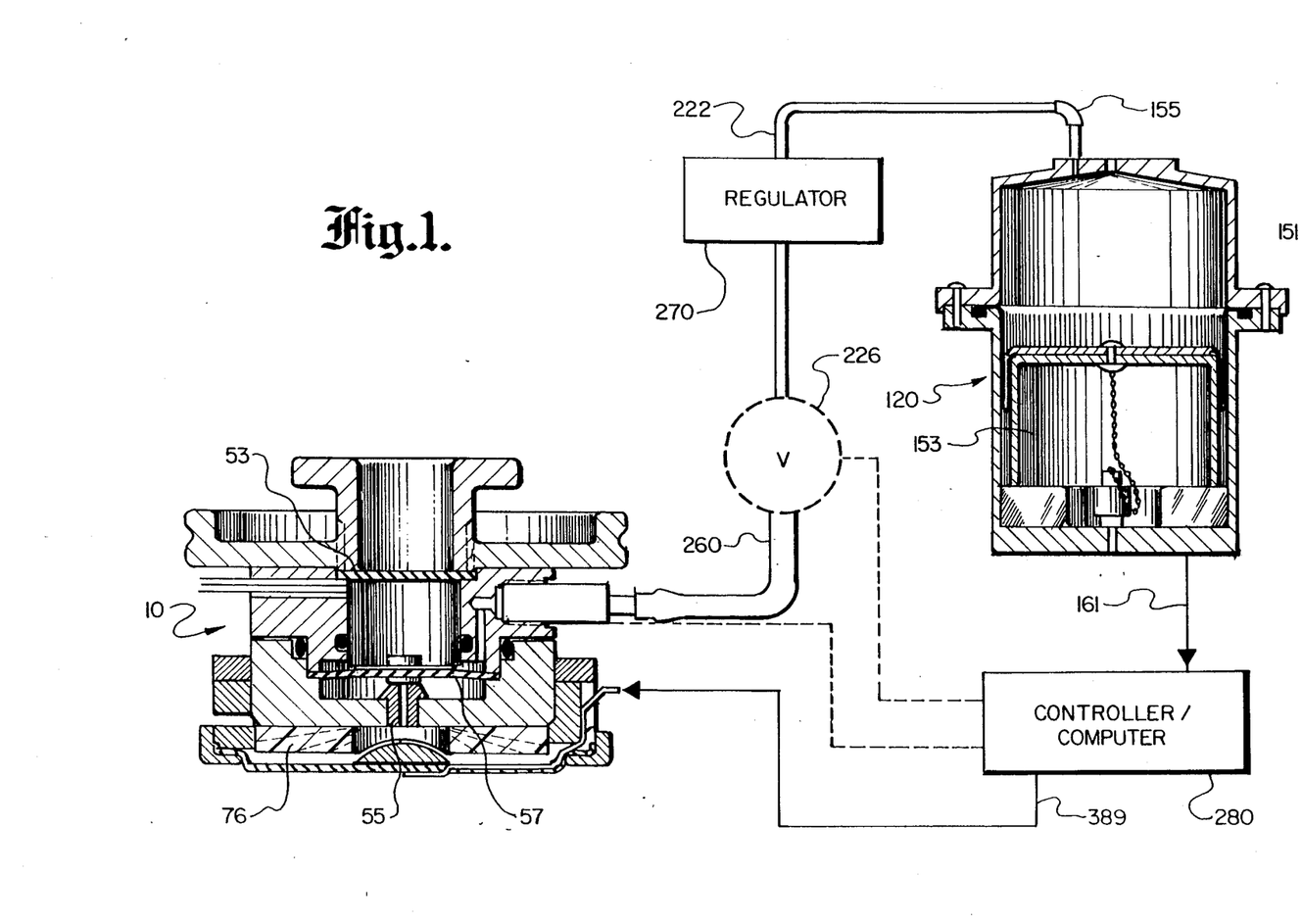
FIG. 1 is a schematic view of the system for cooling skin of the present invention.

Relief valve 160 may also be connected to a pressure switch (shown schematically as switch 168 in FIG. 9) which senses the venting through the relief valve to alert the operator or to signal controller 280 through line 161 (FIG. 1).

Figure 9:
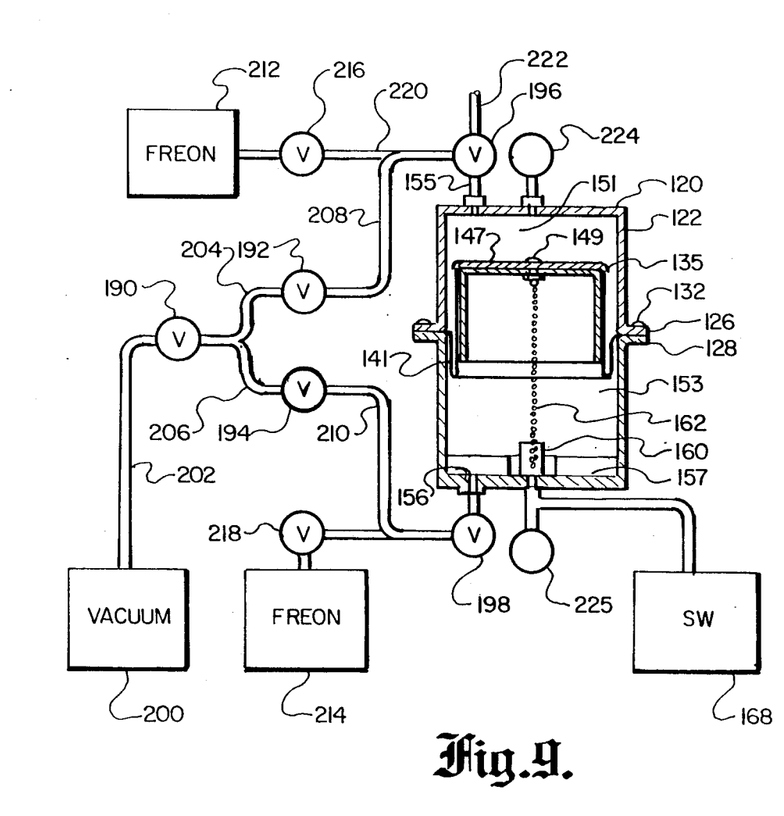
FIG. 9 is a schematic view demonstrating the flow of liquid in the present invention when the container is being filled.

A system for filling vessel 120 in shown in FIG. 9. A vacuum pump is first used to evacuate the inside of vessel 120. First, valves 190, 192, 194, 196, and 198 are opened allowing a free flow path from vacuum pump 200 through line 202, 204 and 208 to outlet 155 into the upper portion 151 of vessel 120 and from line 202 through line 206 and 210 to outlet 156 into bottom portion 153 of the vessel. Container 212 holds fresh $Freon_{114}$, and container 214 holds fresh $Freon_{12}$. Valves 216 and 218 are closed to prevent Freon from containers 212 and 214 from flowing lines 220 and 222 into vacuum pump 200.

When vacuum pump 200 completely evacuates vessel 120, valves 190, 192 and 194 are closed to isolate the vessel from the vacuum pump and to segregate upper portion 151 from lower portion 153. Three way valve 196 positioned to open line 220 to line 155 and closing off line 222, and valve 216 are then opened allowing $Freon_{114}$ from container 112 to flow into and fill upper portion 151 of the vessel. This forces piston 135 downward and allows cavity 151 to be maximized with full fill fluid in the liquid phase only. Valves 216 and 196 are then closed. Next, valves 218 and 198 are opened and a predetermined volume of Freon$_{12}$ from container 214 flows into the lower portion 153. With valve 198 closed, line 210 can be removed. Valve 196 is a two position valve, and it is moved to direct liquid in upper portion 151 into line 222 where it flows ultimately to the heat exchanger. By blocking out the filling position of valve 196, line 220 can be detached from that valve.

For secondary monitoring of the condition of the vessel, two pressure meters 224 and 225 (FIG. 9) may be provided. These may also be combined with relief valves that allow either of cavities 151 or 153 to be vented in the event of an over-pressure malfunction.

Figures 11, 12:
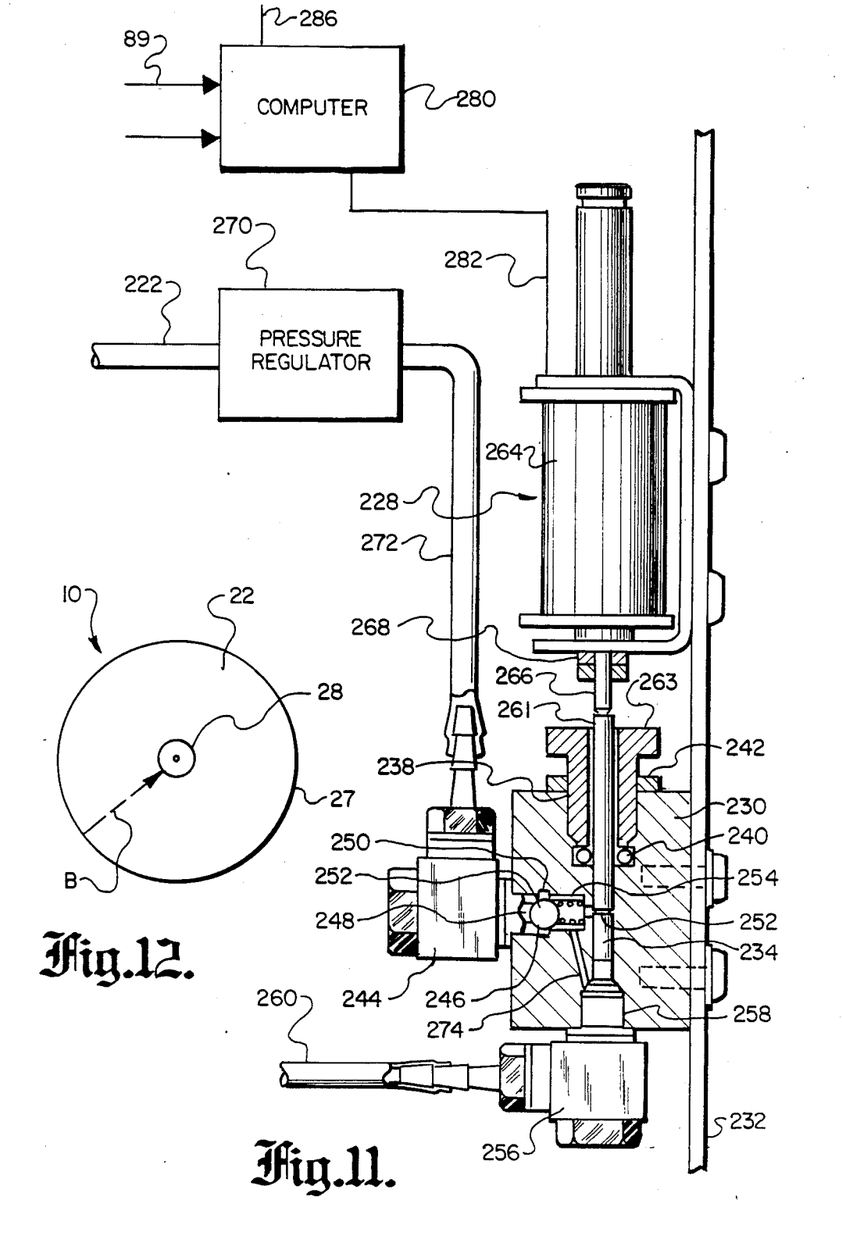
FIG. 11 is a front view partially in section of a liquid injector pump that can be used in a modified version of the second embodiment of the present invention.
FIG. 12 is a bottom view of the heat exchanger of the present invention without details.

5. Liquid Injection and Control: When the liquid Freon$_{114}$ flows out of vessel 120 it must be controlled for proper injection into the heat exchanger. The first embodiment (FIGS. 2-4) has the valve, which controls the flow of Freon$_{114}$, built into the heat exchanger body. Its operation has been explained earlier. The second embodiment (FIG. 5) has outside control from either a high-speed valve (FIG. 1), which is not described in detail, or from an injector, a miniature, solenoid-driven injector pump 228 (FIG. 11).

Pump 228 comprises a main body 230 which is attachable to housing wall 232. The housing for the entire device (not shown in detail) stores many of the parts of the invention. Body 230 has a central opening 234 extending vertically through the body. A threaded gland 236 is received in threaded opening 238 at the top of central opening 234 against O-ring 240. Locking nut 242 secures gland 236 in place.

Inlet fitting 244 is threaded into side opening 246. Spring 254 normally urges check ball valve 252 against seat 250 to prevent fluid flow from central opening 234 back through channel 248 of inward fitting 244. Outlet fitting 256 is threaded into threaded opening 258. Liquid from central opening 234 flows through outlet fitting 256 through line 260 to the inlet fitting 343 of heat exchanger 310 (FIG. 5).

Pin 261 extends through central opening 262 of gland 236 and into central opening 234 of body 230. Solenoid 264 is also mounted to housing wall 232 above body 230 (FIG. 11). Shaft 266, which is movable by solenoid 264, is mounted above and in contact with the upper portion of pin 261. A pair of locking nuts 268 are threaded on shaft 266 and allow the position that shaft 266 extends out of solenoid 264 to be changed, which in turn raises or lowers the position of pin 261.

Liquid Freon$_{114}$ in line 222 (FIG. 11) is at approximately 90 psi. It is easier to work with a liquid at a slightly lower pressure. Therefore, pressure regulator 270 (see also FIG. 1) is interposed in line 222 and lowers the liquid pressure to about 52 psi (269 cm of Hg). The pressure regulator also compensates for changes in the pressure of the liquid Freon caused by changes in the ambient temperature. From pressure regulator 270, the Freon flows through hose 272 into inlet fitting 244 (FIG. 11). If the pressure in hose 260 and in opening 234 (below the bottom of pin 261) is less than the pressure in line 272, the liquid moves check valve 252 against spring 254 until the pressure in hose 260 and opening 234 is the same as pressure in inlet fitting 244. The pressure sensitive valve 354 in the heat exchanger (FIG. 5) is designed to keep the liquid at a predetermined pressure; liquid does not flow unless the force of the liquid overcomes the spring force on the check valve.

When the pressure inside opening 234, fitting 256 and line 260 equalizes, solenoid 264 must drive pin 261 downward in opening 234 thereby increasing the pressure of the liquid within hose 260, fitting 256 and opening 234 to inject fluid past pressure sensitive valve 354 in heat exchanger 310. Check valve 252 prevents the back-flow of the liquid into inlet fitting 244.

Remember that the system is at equilibrium when the pressure of the liquid at pressure sensitive valve 354 of heat exchanger 310 (FIG. 4) is just slightly less than the pressure necessary to open the pressure sensitive valve. Because the liquid is incompressible, the amount of liquid that is driven through pressure sensitive valve 354 corresponds to the volume reduction in opening 234 caused by the movement pin 261. This volume reduction is, of course, a function of the diameter of opening 234 and the length of travel of pin 261. The volume can be modified by changing the rest position of the pin by using adjusting nuts 268 to position shaft 266 of solenoid 264 (FIG. 11).

Pump or injector 228 allows precise control of the volume of fluid ultimately injected into the heat exchanger. It controls volume of liquid by directly controlling the volume entering line 260. Volume can be controlled indirectly by using a high-speed valve 226 (FIG. 1) in the connecting means between vessel 120 and heat exchanger 310 or by use of the solenoid valve in the heat exchange body 11 (FIGS. 2-4). By knowing the pressure of the low-boiling point upstream from valve 226 and the various dimensions of the tubing and the equilibrium pressure, one can calculate or determine by experimentation how long a high speed valve should remain open to dispense the desired amount of liquid.

6. General System Operation: The systems operate in the following fashions. The person to be tested is normally in a room where the air temperature ranges from 68° F. to 78° F. (20° C. to 26° C.). Under those conditions, a normal person's skin temperature is approximately 90° F. (32° C.). In the first embodiment (FIGS. 2-4), computer 280 (FIG. 1) signals solenoid 53 (FIGS. 3, 4) to open so that Freon$_{114}$ flows through orifice 40 of heat exchanger 10. After a chosen duration that is long enough to allow a shot of liquid to flow into heat exchanger chamber 76, computer 280 signals solenoid 53 to release plate 34, which closes orifice 40. Computer 280 continues to signal the solenoid 53 to pulse or stay energized. The temperature of this skin, which is measured by thermocouple 27 (FIG. 3), decreases. The thermocouple is attached to circuitry (not shown) that sends a signal through line 389 (FIGS. 1 and 9) to computer 280. When the computer determines that the skin temperature has reached the predetermined minimum, solenoid 53 stops pulsing, which turns "off" heat exchanger 10 (as soon as the small amount of Freon$_{114}$ vaporizes).

In the other embodiment, computer 280 (FIG. 1) signals valve 226 (FIG. 1) to open or signals solenoid 264 (FIG. 11) to pump Freon$_{114}$ through outlet 256 and hose 260 (FIG. 11) into the heat exchanger 310. After a chosen duration that is long enough to allow a shot of liquid to flow past pressure sensitive valve 254, computer 280 signals valve 226 to close or signals solenoid 264 through line 282 to cease its current flow so that shaft 266 of the solenoid and pin 260 can withdraw to their initial positions. The pressure in opening 234 (FIG. 11) is then less than the pressure in line 272 so that liquid Freon$_{114}$ flows through ball valve 252 and passageway 274 into opening 234 until the pressure in line 272 and opening 234 equalizes.

In all embodiments, one predetermines a pulse frequency and duration, which is chosen with regard to many factors such as the desired rate of cooling, the time that it takes to transmit a pressure pulse from the upstream end of the hose 260 to pressure sensitive valve 354, which in turn is dependent on the length and material of the hose (not a factor in the first embodiment or FIGS. 2-4).

In the second embodiments, computer 280 continues either to open valve 226 or to pulse solenoid 264 while the temperature of this skin decreases. When the computer determines that the skin temperature decreased sufficiently, valve 226 closes or solenoid 264 stops pulsing, which turns "off" heat exchanger 310.

The capillary bed then warms the skin. As the blood flow monitoring method is currently intended to be practiced when the skin is warmed to 78° F. (or some other value determined by medical tests), as indicated by thermocouple 386 sensing that temperature, the computer begins signaling valve 226 to open (or solenoid 264 to pulse), which causes the low-boiling point liquid to flow into the heat exchanger. The cooling/rewarming cycles continue through a predetermined number, sufficient for accuracy.

An approximate temperature range for all embodiments is 78° F. to 73° F. (26° C. to 23° C.). A 5° F. bandwidth was chosen primarily for practical considerations. It takes longer to cool the skin over a greater bandwidth and longer still for the capillary blood flow to return the skin temperature to the upper temperature limit. A much smaller bandwidth creates difficulty in measuring minute temperature changes precisely over the time period of one cycle. The minimum temperature 73° F. is sufficiently low that there is some effect on the capillary bed. If the device operates closer to normal room temperature, the system may react somewhat erratically. Thus, the present invention does not lower the skin temperature to 85° F. and allow it to rise again to its normal 90° F. temperature which would take a long time. Also, changes in room temperature may have a greater effect as the operating range approaches that of normal skin temperature. It may, however, be possible to operate at a higher temperature range, or even at a lower temperature bandwidth.

On each cycle, the computer receives data from line 389 and records the temperature change and rate at which the change takes place. The results of the time-temperature relationship may be displayed either in analog or digital form, or the information may be mathematically manipulated to yield a cardio-thermal index (CTI). The parent application discusses several ways of mathematically manipulating the output to yield a CTI.

The temperature range is also above the minimum temperature that the heat exchanger can attain. By using Freon$_{114}$, the boiling point of Freon$_{114}$ at standard atmospheric pressure is approximately 39° F. (4° C.). Therefore, the minimum temperature that the system can attain is approximately that temperature. The system should not operate below freezing because it could cause localized skin damaged or discomfort. Operating in the 40° F. range is undesirable because it takes longer to cool the skin from its normal 90° F. temperature to the lower temperature and because the lower temperature may create anomalies in readings as the body reacts to more severe cold.

Returning to the design of the heat exchanger, it provides relatively uniform cold in a small-diameter circular area. Irrespective of the orientation of the heat exchanger at a given location, there will be a blood flow through the capillary bed which averages to a vector B (FIG. 12) through the center of disk 22 where thermocouple 27 is located. Thus, when cooling ceases over the area of disk 22, the blood flow begins warming the skin along vector B. The system is accurate because vector B can be in any radial orientation on disk 22. On average the vector passes from the edge of disk 22 through the center of thermocouple 22 so that the blood always has the same distance to travel to warm the skin.

Figure 14:
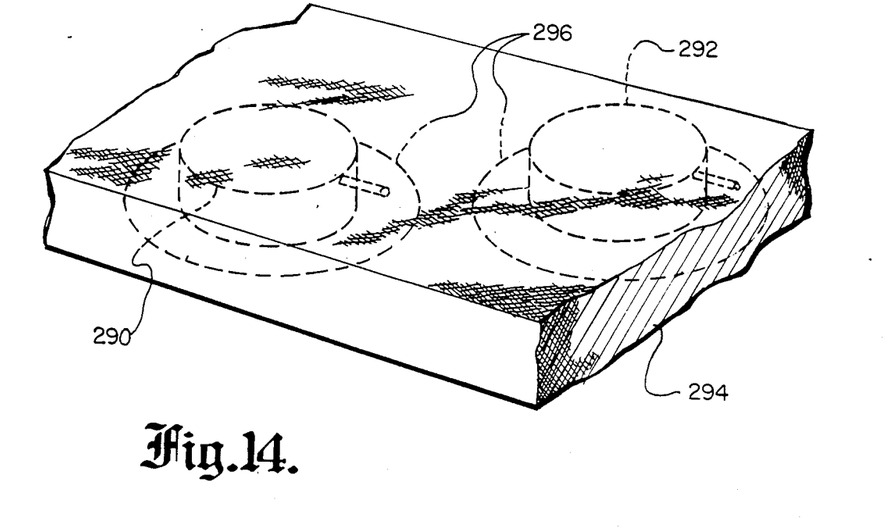
FIG. 14 is a perspective view of cooling fabric, which utilizes the heat exchanger and systems of this invention.

7. Other Use for Heat Exchanger: The heat exchanger of the present invention has been described particularly with regard to the method of blood flow monitoring described. The heat exchanger, however, has numerous other uses, one of which is described here. U.S. Pat. No. 3,479,838 to Bitterly (1969) discloses a cooling fabric for a suit, primarily for use in the vacuum of outer space. A liquid is injected into a special fabric, and in view of the vacuum of outer space, the liquid boils, cooling the skin. Rather than using the special fabric, the heat exchangers of the present invention could be modified and spaced strategically throughout a sheet of fabric to utilize the cooling effect of the heat exchangers at ambient pressures. FIG. 14 represents one possible system for accomplishing that end.

A pair of heat exchangers 290, 292 are embedded in a sheet of fabric 294 (FIG. 14). The heat exchangers operate on the same principal as heat exchanger 10 or 310 (FIGS. 2-5) with some minor exceptions. For cooling fabric, precise temperature control is unnecessary, but in medical applications, the heat exchanger is designed for precise temperature control in the range of less then 0.1° F. (0.06° C.). For a cooling suit, a 5° F. (2.8° C.) variation may be sufficient.

The heat exchangers shown in FIGS. 2-5 are miniaturized. In the medical application, it is unnecessary to cool a large area of skin; it is best to localize the cooling. It is better to cool a larger area of skin in the cooling suit application. Therefore, the size of the disk and the associated valves are increased. A large heat conductive layer, thin aluminum sheets 296, may also be placed immediately below the disk extending outward from it so that body heat from a larger area will be conducted to the cooling heat exchanger.

With the greater diameter of the heat exchanger of FIG. 14, one may reorient the internal check valve to a horizontal orientation so that the height of the unit is minimized and the cooling suit made less bulky. One may vary the spacing of the heat exchangers depending on the portion of the body that the fabric is intended to cover. It is known, for example, that a person's head radiates more heat then other portion of the body. The heat exchangers could be more concentrated in a cap or head band than they would be in a shirt or pants. If the cooling suit is to be used in certain occupations where the worker wearing the suit is exposed to a localized source of heat, more heat exchangers could be concentrated in the body region closer to the heat source. For example, foundry workers may benefit from increased cooling at the chest and abdomen, but race car drivers may be exposed to radiant energy from behind and will find more heat exchangers per area at their back to be of benefit.

As with the medical embodiment (FIGS. 2-5), the cooling suit system is fed by separate lines carrying low-boiling point liquid to the heat exchangers. Temperature sensors associated with each heat exchanger or with a group of heat exchangers can signal a microprocessor to activate one, a group or several groups of heat exchangers for a certain time period until the temperature sensors respond to the skin cooling and shut the heat exchanger(s) off.

Various other modifications of all of the systems of the present invention will suggest themselves to those of ordinary skill in the art. The invention described in this application meets the objects stated.

I claim:

1. A system for cooling an area of the surface of an object comprising:
   (a) a heat exchanger having a body attachable to the object and a cooling chamber having a cooling surface adapted to be against the object;
   (b) a source of primary fluid having a boiling point below room temperature at standard atmospheric pressure, the source of primary fluid being a vessel; movable divider means in the vessel for dividing the vessel into first and second spaces, the first space adapted to receive the primary fluid, an outlet extending from the first space to the outside of the vessel; the second space adapted to receive a secondary fluid having a vapor pressure higher than the vapor pressure of the primary fluid whereby the vapor of the secondary fluid applies pressure to the movable divider means to pressurize the primary fluid;
   (c) connecting means between the outlet of the source of primary fluid and the cooling chamber of the heat exchanger for transporting the primary fluid from the source to the cooling chamber;
   (d) valve means between the connecting means and the cooling chamber for normally blocking flow of primary fluid from the source to the cooling chamber; and
   (e) signaling means operably connected to the valve means for opening the valve means to pass a controlled amount of primary fluid to the cooling chamber of the heat exchanger where the primary fluid vaporizes to cool the surface of the object.

2. The system of claim 1 wherein the movable divider means comprises a diaphragm extending across the vessel and movable in the vessel in response to changes of the amount of primary and secondary fluid in the first and second spaces, respectively.

3. The system of claim 1 wherein the movable divider means comprises a piston extending across the vessel and movable to change the respective volumes of the first and second spaces as the amount of primary and secondary fluids changes.

4. The system of claim 1 wherein the secondary fluid has a vapor pressure that is at least twice the vapor pressure of the primary fluid.

5. The system of claim 1 wherein at atmospheric pressure, the primary fluid boils at less then 50° F., and the secondary fluid boils at less than 0° F.

6. The system of claim 5 wherein the boiling point of the primary fluid at atmospheric pressure is greater than 32° F.

7. The system of claim 1 wherein the primary fluid is Freon$_{114}$ and the secondary fluid is Freon$_{12}$.

8. The system of claim 1 further comprising release valve means in the second space for venting the secondary fluid from the second space, interconnecting means extending between the release valve means and the movable divider means to open the release valve means when the volume of primary fluid in the first space is below a predetermined minimum of volume as a result of movement of the movable divider means.

9. The system of claim 8 wherein the release valve means has a valve closure member and a valve seat, bias means for urging the valve closure member to a normally closed position, the interconnecting means comprising a flexible connection having two ends, one end of which is attached to the movable divider means and the other end is operably attached to the valve closure member, the flexible connection applying insufficient force to the valve closure member against the urging of the bias means to maintain the closure member in the normally closed position when the divider means is in a position such that the first space is greater than the predetermined volume, the flexible connection pulling on the valve closure member against the urging of the bias means when the movable divider means is in a position such that the first space is less than the predetermined volume whereby the valve closure member is pulled away from the valve seat to open the release valve.

10. A system for cooling an area of the surface of an object comprising:
    (a) a heat exchanger having a body member attachable to the object and a cooling chamber having a cooling surface adapted to be against the object;
    (b) a source of a primary fluid having a boiling point below room temperature at standard atmospheric pressure;
    (c) connecting means between the source of primary fluid and the cooling chamber of the heat exchanger for transporting the primary fluid from the source to the cooling chamber;
    (d) valve means between the connecting means and the cooling chamber for normally blocking flow of primary fluid from the source to the cooling chamber; and
    (e) signaling means operably connected to the valve means for opening the valve means to pass a controlled amount of primary fluid to the cooling chamber of the heat exchanger where the primary fluid vaporizes to cool the surface of the object.

11. The system of claim 10 wherein the cooling chamber is on one side of the body member, conductive surface means mounted to the body member but spaced from the body member for forming a portion of the cooling chamber, the valve means being mounted in the body member, the valve means comprising an orifice extending into the cooling chamber in the path of the flow of primary fluid, and a solenoid having an electromagnet and a spring plate normally biased to cover the orifice to block the flow of fluid to the orifice, the spring plate being attracted to the electromagnet when the electromagnet is energized to permit the fluid to flow through the orifice.

12. The system of claim 11 further comprising ballonet means attached to the heat exchanger, the ballonet means being expandable when air is injected into the ballonet means, positioning means for positioning the heat exchanger on the object to be cooled, connecting means on the positioning means for connecting the ballonet means to the positioning means, means extending from a source of pressurized air to the ballonet means for injecting air into the ballonet means for expanding the ballonet against the connecting means to urge the heat exchanger against the object to be cooled.

13. The system of claim 12 further comprising adjusting means in the body member of the heat exchanger for moving the electromagnet and the spring plate relative to each other to adjust the distance that the spring plate moves when the electromagnet is energized, a portion of the adjusting means extending into the ballonet means.

14. The system of claim 11 further comprising adjusting means in the body member of the heat exchanger for moving the electromagnet and the spring plate relative to each other to adjust the distance that the spring plate moves when the electromagnet is energized.

15. The system of claim 11 further comprising pad means attached to the spring plate to seal the orifice when the spring plate is in its normal position covering the orifice.

16. The system of claim 11 further comprising supporting means attached to the body member for forming part of the cooling chamber and for supporting the conductive surface means, the supporting means including attaching means for attaching the supporting means to the body.

17. The system of claim 16 further comprising backing means substantially filling the chamber for supporting the conductive surface means.

18. The system of claim 16 further comprising wick means from the orifice extending to the conductive surface means for transporting the primary fluid from the orifice to the conductive surface means.

19. The system of claim 18 further comprising backing means substantially filling the chamber for supporting the conductive surface, the wick means extending through the backing means.

20. The system of claim 18 wherein the supporting means comprises a ring, the cooling chamber having outside walls, the inside of the ring forming a portion of the outside walls of the cooling chamber, the body member of the heat exchanger having receiving means on its outside for receiving the supporting means.

21. The system of claim 20 wherein the receiving means comprises a thread on the outside of the body member of the heat exchanger, the ring having a thread engaging the thread on the outside of the body member of the heat exchanger.

22. The system of claim 21 further comprising a lock nut threaded to the thread on the outside of the body member of the heat exchanger against the ring to secure the ring to the body member of the heat exchanger.

23. The system of claim 11 further comprising temperature sensing means on the outside of the conductive surface means for contacting the object to be cooled, and insulation means between the temperature sensing means and the conductive surface means shielding the temperature sensing means from heat flux directly from or to the heat conductive surface means.

24. The system of claim 23 further comprising a first conductor attached to the temperature sensing means and a slip conductor rotatably mounted to the outside of the body member and electrically connected to the first conductor for being electrically connected to an outside conductor.

25. The system of claim 10 wherein the valve means comprises a pressure sensitive valve between the connecting means and the heat exchanger for blocking flow of primary fluid from the source to the heat exchanger except when the pressure of the primary fluid at the pressure sensitive valve is no lower than a predetermined pressure, and control means in the connecting means upstream of the pressure sensitive valve normally blocking the connecting means, the control means in response to a signal from the signaling means passing a controlled amount of primary fluid at a pressure no lower than the pre-determined pressure to the pressure sensitive valve and into the heat exchanger where the primary fluid vaporizes to cool the surface of the object.

26. The system of claim 25 further comprising mounting means in the body member of the heat exchanger for mounting the pressure sensitive valve in the body and passage means extending through the body member from the pressure sensitive valve into the chamber for conducting the primary fluid from the pressure sensitive valve into the chamber.

27. The system of claim 26 wherein the pressure sensitive valve comprises a poppet having a upper portion and a lower portion, the upper portion being mounted above the passage means, a retainer mounted on the upper portion of the poppet, a spring means extending between the retainer and the body of the heat exchanger for urging the upper portion of the poppet upward, the poppet further comprising a closure member seated against the passage means to block the flow of primary fluid into the passage means when the spring means urges the poppet upward to seat the valve closure member.

28. A system for cooling an area of the surface of an object comprising:
 (a) a heat exchanger attachable to the object;
 (b) a source of a primary fluid having a boiling point below room temperature at standard atmospheric pressure;
 (c) connecting means between the source of primary fluid and the heat exchanger for transporting the primary fluid from the source to the heat exchanger;
 (d) pressure sensitive valve means between the connecting means and the heat exchanger for blocking flow of primary fluid from the source to the heat exchanger except when the pressure of the primary fluid at the pressure sensitive valve means is no lower than a given pressure; and
 (e) control means in the connecting means upstream of the pressure sensitive valve means normally blocking the connecting means, the control means operating in response to a signal passing a controlled amount of primary fluid at a pressure no lower than a pre-determined pressure to the pressure sensitive valve means and into the heat exchanger where the primary fluid vaporizes to cool the surface of the object 29. The system of claim 28 wherein the source of primary fluid is a vessel, movable divider means in the vessel for dividing the vessel into first and second spaces, the first space adapted to receive the primary fluid, an outlet extending from the first space to the outside of the vessel, the second space adapted to receive a secondary fluid having a vapor pressure higher than the vapor pressure of the primary fluid whereby the vapor of the secondary fluid applies pressure to the movable divider means to pressurize the primary fluid.

30. The system of claim 29 wherein the movable divider means comprises a diaphragm extending across the vessel and movable in the vessel in response to changes of the amount of primary and secondary fluid in the first and second spaces, respectively.

31. The system of claim 29 wherein the movable divider means comprises a piston extending across the vessel and movable to change the respective volumes of the first and second spaces as the amount of primary and secondary fluid changes.

32. The system of claim 29 wherein the second fluid has a vapor pressure that is at least twice the vapor pressure of the primary fluid.

33. The system of claim 29 further comprising a release valve means in the second space for venting the secondary fluid from the second space, interconnecting means extending between the release valve means and the movable divider means to open the release valve means when the volume of primary fluid in the first space is below a predetermined minimum of volume as a result of movement of the movable divider means.

34. The system of claim 29 wherein the connecting means includes injector means for receiving a controlled volume of the primary fluid from the connecting means and injecting the controlled volume back into the connecting means at a pressure sufficient to force an amount of the primary fluid equal to the control volume into the heat exchanger.

35. The system of claim 34 wherein the injector means comprises a holding chamber attached to the connecting means for receiving the primary fluid; check valve means between the holding chamber and the connecting means for permitting the primary fluid to flow downstream from the connecting means into the holding chamber when the pressure of the primary fluid in the holding chamber is less than the pressure of the primary fluid in the connecting means upstream from the injector means and for blocking the flow of the primary fluid from the holding chamber into the connecting means upstream from the injector means; an outlet from the holding chamber back into the connecting means downstream from the injector means; and volume reduction means in the holding chamber for reducing the volume of the holding chamber to push the primary fluid out of the holding chamber and through the outlet.

36. The system of claim 35 wherein the volume reduction means comprises a piston movable into and out of the holding chamber and drive means attached to the piston for moving the piston into the holding chamber.

37. The system of claim 36 wherein the drive means comprises a solenoid means for driving the piston in response to an electrical signal.

38. The system of claim 37 further comprising wick means from the passage means extending to the conductive surface means for transporting the primary fluid from the passage means to the conductive surface means.

39. The system of claim 38 further comprising backing means substantially filling the chamber for supporting the conductive surface means, the wick means extending through the backing means.

40. The system of claim 28 wherein the heat exchanger comprises a body, a cooling chamber on one side of the body, a conductive surface means mounted to the body but spaced from the body for forming a portion of the cooling chamber, valve mounting means in the body of the heat exchanger for mounting the pressure sensitive valve means in the body, and passage means extending through the body from the pressure sensitive valve means into the chamber for conducting the primary fluid from the pressure sensitive valve means into the chamber.

41. The system of claim 40 further comprising supporting means attached to the body of the heat exchanger for forming part of the chamber and for supporting the conductive surface means, the supporting means including attaching means for attaching the supporting means to the body of the heat exchanger.

42. The system of claim 41 further comprising backing means substantially filling the chamber for supporting the conductive surface means.

43. The system of claim 41 wherein the supporting means comprises a ring, the chamber having outside walls, the inside of the ring forming a portion of the outside walls of the chamber, the body of the heat exchanger having receiving means on the outside for receiving the supporting means.

44. The system of claim 43 wherein the receiving means comprises a thread on the outside of the body of the heat exchanger, the ring having a thread engaging the thread on the outside of the body of the heat exchanger.

45. The system of claim 44 further comprising a lock nut threaded to the thread on the outside of the body of the heat exchanger against the ring to secure the ring to the body of the heat exchanger.

46. The system of claim 40 further comprising a removable vent means in the body extending into the valve mounting means for venting gas in the connecting means.

47. The system of claim 40 wherein the pressure sensitive valve means comprises a poppet having a upper portion and a lower portion, the upper portion being mounted above the passage means, a retainer mounted on the upper portion of the poppet, a spring means extending between the retainer and the body of the heat exchanger for urging the upper portion of the poppet upward, the poppet further comprising a closure member seated against the passage means to block the flow of primary fluid into the passage means when the spring urges the poppet upward to seat the valve closure member.

48. The system of claim 40 further comprising temperature sensing means on the outside of the conductive surface means for contacting the object to be cooled, and insulation means between the temperature sensing means and the conductive surface means shielding the temperature sensing means from heat flux directly from or to the conducting surface means.

* * * * *